US008871199B2

(12) United States Patent
Centeno

(10) Patent No.: US 8,871,199 B2
(45) Date of Patent: Oct. 28, 2014

(54) COMPOSITIONS AND METHODS TO PROMOTE IMPLANTATION AND ENGRAFMENT OF STEM CELLS

(71) Applicant: Regenerative Sciences, LLC, Broomfield, CO (US)

(72) Inventor: Christopher J. Centeno, Broomfield, CO (US)

(73) Assignee: Regenerative Sciences, LLC, Broomfield, CO (US)

( * ) Notice: Subject to any disclaimer, the term of this patent is extended or adjusted under 35 U.S.C. 154(b) by 0 days.

(21) Appl. No.: 13/685,527

(22) Filed: Nov. 26, 2012

(65) Prior Publication Data

US 2013/0084341 A1    Apr. 4, 2013

Related U.S. Application Data

(63) Continuation of application No. 12/809,445, filed as application No. PCT/US2008/087452 on Dec. 18, 2008, now abandoned.

(60) Provisional application No. 61/014,987, filed on Dec. 19, 2007.

(51) Int. Cl.
| *A01N 63/00* | (2006.01) |
| *A61K 39/395* | (2006.01) |
| *A61K 35/12* | (2006.01) |
| *A61K 31/7004* | (2006.01) |
| *A61K 31/05* | (2006.01) |
| *A61K 35/14* | (2006.01) |
| *A61K 38/19* | (2006.01) |
| *A61K 35/16* | (2006.01) |
| *A61K 38/36* | (2006.01) |
| *A61K 45/06* | (2006.01) |

(52) U.S. Cl.
CPC ............ *A61K 35/19* (2013.01); *A61K 31/7004* (2013.01); *A61K 31/05* (2013.01); *A61K 38/19* (2013.01); *A61K 35/16* (2013.01); *A61K 38/363* (2013.01); *A61K 45/06* (2013.01)
USPC ....... 424/93.7; 424/145.1; 424/520; 424/532; 424/577

(58) Field of Classification Search
None
See application file for complete search history.

(56) References Cited

U.S. PATENT DOCUMENTS

| 4,832,044 A | 5/1989 | Garg |
| 5,145,676 A | 9/1992 | Fahey et al. |
| 5,165,938 A | 11/1992 | Knighton |
| 5,198,357 A | 3/1993 | Holmovist et al. |
| 5,226,914 A | 7/1993 | Caplan et al. |
| 5,486,359 A | 1/1996 | Caplan et al. |
| 5,693,341 A | 12/1997 | Schroeder et al. |
| 5,736,396 A | 4/1998 | Bruder et al. |
| 5,749,874 A | 5/1998 | Schwartz |
| 5,769,899 A | 6/1998 | Schwartz et al. |
| 5,770,215 A | 6/1998 | Moshyedi |
| 5,842,477 A | 12/1998 | Naughton et al. |
| 6,200,606 B1 | 3/2001 | Peterson et al. |
| 6,530,956 B1 | 3/2003 | Mansmann |
| 6,623,733 B1 | 9/2003 | Hossainy et al. |
| 6,699,471 B2 | 3/2004 | Radice et al. |
| 6,699,484 B2 | 3/2004 | Whitmore et al. |
| 6,835,377 B2 | 12/2004 | Goldberg et al. |
| 6,872,567 B2 | 3/2005 | Thomas et al. |
| 7,229,959 B1 | 6/2007 | Drohan et al. |
| 7,905,863 B1 | 3/2011 | Forrest |
| 8,088,119 B2 | 1/2012 | Saal et al. |
| 8,277,437 B2 | 10/2012 | Saal et al. |
| 2002/0110544 A1 | 8/2002 | Goldberg et al. |
| 2003/0050709 A1 | 3/2003 | North et al. |
| 2003/0224411 A1 | 12/2003 | Stanton et al. |
| 2004/0078077 A1 | 4/2004 | Binette et al. |
| 2004/0136968 A1 | 7/2004 | Zheng et al. |
| 2004/0229786 A1 | 11/2004 | Attawia et al. |
| 2004/0229878 A1 | 11/2004 | DiMauro et al. |
| 2004/0235166 A1 | 11/2004 | Prockop et al. |
| 2005/0019865 A1 | 1/2005 | Kihm et al. |
| 2005/0038520 A1 | 2/2005 | Binette et al. |
| 2005/0100536 A1 | 5/2005 | Mishra |
| 2005/0118230 A1 | 6/2005 | Hill et al. |
| 2005/0205498 A1 | 9/2005 | Sowemimo-Coker et al. |
| 2005/0276792 A1 | 12/2005 | Kaminski et al. |
| 2006/0073124 A1 | 4/2006 | Garcia Castro et al. |
| 2006/0128016 A1 | 6/2006 | Tokushima et al. |
| 2006/0275273 A1 | 12/2006 | Seyedin et al. |

(Continued)

FOREIGN PATENT DOCUMENTS

| KR | 2003 024028 | 3/2003 |
| WO | WO 97/34614 | 9/1997 |

(Continued)

OTHER PUBLICATIONS

Ries et al.; Blood. (2007); 109:4055-4063.*
Centeno et al. (2008) The American Journal of Case Reports 9:201-206 "Increased Knee Cartilage Volume in Degenerative Joint Disease using Percutaneously Implanted, Autologous Mesenchymal Stem Cells, Platelet Lysate and Dexamethasone".
Centeno et al. (2008) Pain Physician 11(3):343-353 "Increased Knee Cartilage Volume in Degenerative Joint Disease using Percutaneously Implanted, Autologous Mesenchymal Stem Cells".

(Continued)

*Primary Examiner* — Jeffrey T Palenik
(74) *Attorney, Agent, or Firm* — Swanson & Bratschun, L.L.C.

(57) ABSTRACT

Tissue repair in-vivo depends on acute inflammation, but in many clinical situations the other major components of healing such as blood supply, anabolic hormones, growth factors, and stem cells are lacking. This invention includes compositions consisting of an agent which induces an inflammatory healing response combined with an autologous platelet lysate at a specific concentration which may have demonstrated in-vitro abilities to expand autologous tissue repair cells.

11 Claims, No Drawings

(56) References Cited

U.S. PATENT DOCUMENTS

| | | | |
|---|---|---|---|
| 2007/0087032 | A1 | 4/2007 | Chang et al. |
| 2007/0122904 | A1 | 5/2007 | Nordon |
| 2007/0128722 | A1 | 6/2007 | Lin et al. |
| 2008/0038233 | A1 | 2/2008 | Freemont et al. |
| 2009/0010896 | A1 | 1/2009 | Centeno et al. |
| 2009/0208464 | A1 | 8/2009 | Centeno |
| 2009/0274665 | A1* | 11/2009 | Akabutu et al. ............ 424/93.7 |
| 2010/0168022 | A1 | 7/2010 | Centeno |
| 2011/0052533 | A1 | 3/2011 | Centeno |
| 2011/0054929 | A1 | 3/2011 | Centeno |
| 2011/0200642 | A1 | 8/2011 | Centeno |
| 2011/0245804 | A1 | 10/2011 | Centeno |
| 2011/0276001 | A1 | 11/2011 | Centeno et al. |
| 2013/0108593 | A1 | 5/2013 | Centeno |

FOREIGN PATENT DOCUMENTS

| | | |
|---|---|---|
| WO | WO 98/51317 | 11/1998 |
| WO | WO 01/80865 | 11/2001 |
| WO | WO 2004/067704 | 8/2004 |
| WO | WO 2005/046761 | 5/2005 |
| WO | WO 2005/085421 | 9/2005 |
| WO | WO 2007/087519 | 8/2007 |
| WO | WO 2008/034803 | 3/2008 |
| WO | WO 2009/006161 | 1/2009 |
| WO | WO 2009/085969 | 7/2009 |
| WO | WO 2009/114785 | 9/2009 |
| WO | WO 2009/124192 | 10/2009 |
| WO | WO 2010/065854 | 6/2010 |
| WO | EP 2257176 | 9/2013 |

OTHER PUBLICATIONS

Centeno et al. (2011) Bioengineering & Biomedical Science S2:007 "A Case Series of Percutaneous Treatment of Non-Union Fractures with Aulogous, Culture Expanded, Bone Marrow Derived, Mesenchymal Stem Cells and Platelet Lysate".

Xian and Foster (2006) Current Stem Cells Research and Therapy 1:213-229 "Repair of Injured Articular and Growth Plate Cartilage Using Mesenchymal Stem Cells and Chondrogenic Gene Therapy".

Acosta et al (2005) "The Potential Role of Mesenchymal Stem Cell Therapy for Intervertebral Disc Degeneration: A Critical Overview" Neurosurg. Focus 19(3):E4.

Ahuja et al (1995) "Identification of Two Subpopulations of Rat Monocytes Expressing Disparate Molecular Forms and Quantities of CD43" Cell Immunol. 163(1):59-69.

Alhadlaq and Mao (2004) "Mesenchymal Stem Cells: Isolation and Therapeutics" Stem Cells Dev. 13(4):436-448.

Ando et al (2007) "Cartilage repair using an in vitro generated scaffold-free tissue-engineered construct derived from porcine synovial mesenchymal stem cells" Biomaterials 1-9. Available Website: www.sciencedirect.com.

Anitua et al (2004) "Autologous Platelets as a Source of Proteins for Healing and Tissue Regeneration" Thromb. Haemost. 91:4-15.

Avascular Necrosis in patient education of Illinois Bone and Joint Institute. 2003 downloaded from the hipdoc.com/avas.htm. p. 1-2.

Baecher-Allan et al (2005) "Functional Analysis of Highly Defined, FACS-Isolated Populations of Human Regulatory CD4+CD25+ T Cells" Clinical Immunology 115:10-18.

Barry (2003) "Mesenchymal Stem Cell Therapy in Joint Disease" Novartis Found. Symp. 249:86-102, 170-4, 239-41.

Bensaïd et al (2003) "A Biodegradable Fibrin Scaffold for Mesenchymal Stem Cell Transplantation" Biomaterials 24:2497-2502.

Bernardo et al (2007) "Optimization of In Vitro Expansion of Human Multipotent Mesenchymal Stromal Cells for Cell-Therapy Approaches: Further Insights in the Search for a Fetal Calf Serum Substitute" J. Cell. Physiol. 211:121-130.

Billard et al (2000) "Switch in the Protein Tyrosine Phosphatase Associated with Human CD100 Semaphorin at Terminal B-Cell Differentiation Stage" Blood 95(3):965-972.

Bircher et al (1988) "Discitis Following Lumbar Surgery" Spine 13(1):98-102.

Borner and Follath (1989) "Antibiotic Therapy and Long-Term Outcome in Patients with Vertebral Osteomyelitis" Schweiz Med. Wochenschr. 119(1):19-21 (German, English Abstract Only).

Brisby et al (2004) "Cell Therapy for Disc Degeneration-Potentials and Pitfalls" Orthop. Clin. North Am. 35(1):85-93.

Buckwalter and Mankin (1998) "Articular Cartilage: Degeneration and Osteoarthritis, Repair, Regeneration, and Transplantation" AAOS Instr. Course Lect. 47:487-504.

Bühring et al (1999) "The Monoclonal Antibody 97A6 Defines a Novel Surface Antigen Expressed on Human Basophils and Their Multipotent and Unipotent Progenitors" Blood 94(7):2343-2356.

Caligiuri et al (1990) "Functional Consequences of Interleukin 2 Receptor Expression on Resting Human Lymphocytes. Identification of a Novel Natural Killer Cell Subset with High Affinity Receptors" J. Exp. Med. 171:1509-1526.

Caplan and Bruder (2001) "Mesenchymal Stem Cells: Building Blocks for Molecular Medicine in the 21st Century" Trends Mol. Med. 7(6):259-264.

Caplan (1991) "Mesenchymal Stem Cells" J. Orthop. Res. 9(5):641-650.

Cashman et al (1990) "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-Beta" Blood 75(1):96-101.

Cassiede et al (1996) "Osteochondrogenic Potential of Marrow Mesenchymal Progenitor Cells Exposed to TGF-β1 or PDGF-BB as Assayed In Vivo and In Vitro" J. of Bone and Miner. Res. 11(9):1264-1273.

Castro et al (2002) "Failure of Bone Marrow Cells to Transdifferentiate into Neutral Cells In Vivo" Science 297:1299.

Centeno et al (2006) "Partial Regeneration of the Human Hip Nucleated Cell Transfer: A Case Study" Pain Physician 9:253-256.

Centeno et al (2008) "Regeneration of meniscus cartilage in a knee treated with percutaneously implanted autologous mesenchymal stem cells" Medical Hypotheses 71:900-908.

Centeno and Faulkner (2012) "The Use of Mesenchymal Stem Cells in Orthopedics" Stem Cells and Cancer Stem Cells 1:173-179.

Charalambous et al (2003) "Septic Arthritis Following Intra-Articular Steroid Injection of the Knee—a Survey of Current Practice Regarding Antiseptic Technique used During Intra-Articular Steroid Injection of the Knee" Clin. Rheumatol. 22:386-390.

Chazerain et al (1999) "Septic Hip Arthritis After Multiple Injections into the Joint of Hyaluronate and Glucocorticoid" Rev. Rhum. Engl. Ed. 66(7-9):436-437.

Crisostomo et al (2006) "High Passage Number of Stem Cells Adversely Affects Stem Cell Activation and Myocardial Protection" Shock 26(6):575-580.

D'Ippolito et al (1999) "Age-Related Osteogenic Potential of Mesenchymal Stromal Stem Cells from Human Verterbral Bone Marrow" J. Bone Miner. Res. 14(7):1115-122.

Dall et al (1987) "Postoperative Discitis. Diagnosis and Management" Clin. Orthop. Relat. Res. 224:138-146.

Del Curling et al (1990) "Changing Concepts in Spinal Epidural Abscess: A Report of 29 Cases" Neurosurgery 27(2):185-192.

Deschaseaux et al (2003) "Direct Selection of Human Bone Marrow Mesenchymal Stem Cells Using an Anti-CD49a Antibody Reveals Their $CD45^{med,low}$ Phenotype" British Journal of Haematology 122:506-517.

Doucet et al (2005) "Platelet Lysates Promote Mesenchymal Stem Cell Expansion: A Safety Substitute for Animal Serum in Cell-Based Therapy Applications" J. Cell. Physiol. 205:228-236.

Elghetany and Patel (2002) "Assessment of CD24 Expression on Bone Marrow Neutrophilic Granulocytes: CD24 is a Marker for the Myelocytic Stage of Development" Am. J. Hematol. 71:348-349.

Fang et al (2004) "Biocompatibility Studies on Fibrin Glue Cultured with Bone Marrow Mesenchymal Stem Cells In Vitro" J. of Huazhong. Univ. of Sci. Technolog. Med. Sci. 24(3):272-274.

Fiedler et al (2002) "BMP-2, BMP-4, and PDGF-bb Stimulate Chemotactic Migration of Primary Human Mesenchymal Progenitor Cells" J. Cell. Biochem. 87:305-312.

(56) References Cited

OTHER PUBLICATIONS

Fiedler et al (2004) "To Go or Not to Go: Migration of Human Mesenchymal Progenitor Cells Stimulated by Isoforms of PDGF" J. Cell. Biochem. 93:990-998.

Fortier et al (1998) "Isolation and Chondrocytic Differentiation of Equine Bone Marrow-Derived Mesenchymal Stem Cells" Am. J. Vet. Res. 59(9):1182-1187.

Fraser et al (1993) "Each Hypersensitive Site of the Human Beta-Globin Locus Control Region Confers a Different Developmental Pattern of Expression on the Globin Genes" Genes & Development 7:106-113.

Fujiwara et al (1994) "Acute Purulent Discitis with Epidural Abscess of the Cervical Spine in an Adult" Neurol. Med. Chir. (Tokyo) 34(6):382-384.

Gajdusek et al (1993) "Basic Fibroblast Growth Factor and Transforming Growth Factor Beta-1: Synergistic Mediators of Angiogenesis In Vitro" J. Cell. Physiol. 157(1):133-144.

Gazzit et al (1995) "Purified $CD34^+$ $Lin^-$ $Thy^+$ Stem Cells do Not Contain Clonal Myeloma Cells" Blood 86(1):381-389.

Gibson and Waddell (2005) "Surgery for Degenerative Lumbar Spondylosis: Updated Cochrane Review" Spine 30(20):2312-2320.

Gruber and Hanley (2003) "Recent Advances in Disc Cell Biology" Spine 28(2):186-193.

Gruber et al (2004) "Platelet-Released Supernatants Increase Migration and Proliferation, and Decrease Osteogenic Differentiation of Bone Marrow-Derived Mesenchymal Progenitor Cells Under In Vitro Conditions" Platelets 15(1):29-35.

Gustafson et al (1989) "Further Investigations into the Potentiation of Infection by Intra-Articular Injection of Polysulfated Glycosaminoglycan and the Effect of Filtration and Intra-Articular Injection of Amikacin" Am. J. Vet. Res. 50(12):2018-2022.

Hickstein et al (1992) "Identification of the Promoter of the Myelomonocytic Leukocyte Integrin CD11b" Proc. Natl. Acad. Sci. USA 89(6):2105-2109.

Hip Replacement Surgery. John Hopkins Medicine. Downloaded on Jul. 14, 2012 from www.hopkinsmedicine.org/healthlibrary/conditions/adult/orthopaedic_disorders/hip_replacement_surger_85, P01372. p. 1-4.

Hirschi et al (1999) "Endothelial Cells Modulate the Proliferation of Mural Cell Precursors Via Platelet-Derived Growth Factor-BB and Heterotypic Cell Contact" Circ. Res. 84(3):298-305.

Hoelscher et al (2000) "Effects of Very High Antibiotic Concentrations on Human Intervertebral Disc Cell Proliferation, Viability, and Metabolism In Vitro" Spine 25(15):1871-1877.

Huang and Terstappen (1994) "Formation of Haematopoietic Microenvironment and Haematopoietic Stem Cells from Single Human Bone Marrow Stem Cells" Nature 368(6472):664.

Huss (2000) "Perspectives on the Morphology and Biology of CD34-Negative Stem Cells" J. Hematother. Stem Cell Res. 9:783-793.

Iversen et al (1992) "Prognosis in Postoperative Discitis, A Retrospective Study of 111 Cases" Acta Orthop. Scand. 63(3):305-309.

Johnstone and Yoo (1999) "Autologous Mesenchymal Progenitor Cells in Articular Cartilage Repair" Clin. Orthop. Relat. Res. 367 Suppl:S156-162.

Kambin and Schaffer (1989) "Percutaneous Lumbar Discectomy Review of 100 Patients and Current Practice" Clin. Orthop. Relat. Res. 238:24-34.

Kang et al (2005) "Role of c-Jun N-Terminal Kinase in the PDGF-Induced Proliferation and Migration of Human Adipose Tissue-Derived Mesenchymal Stem Cells" J. Cell. Biochem. 95:1135-1145.

Kaps et al (2002) "Human Platelet Supernatant Promotes Proliferation but Not Differentiation of Articular Chondrocytes" Med. Biol. Eng. Comput. 40(4):485-490.

Katz et al (1987) "Effect of Platelet-Derived Growth Factor on Enriched Populations of Haemopoietic Progenitors from Patients with Chronic Myeloid Leukaemia" Leuk. Res. 11(4):339-344.

Kilian et al (2004) "Effects of Platelet Growth Factors on Human Mesenchymal Stem Cells and Human Endothelial Cells In Vitro" Eur. J. Med. Res. 9(7):337-344.

Kirshenbaum et al (1999) "Demonstration that Human Mast Cells Arise from a Progenitor Cell Population that is CD34+, c-kit+, and Expresses Aminopeptidase N (CD13)" Blood 94:2333-2342.

Kitoh et al (2004) "Transplantation of Marrow-Derived Mesenchymal Stem Cells and Platelet-Rich Plasma During Distraction Osteogenesis—a Preliminary Result of Three Cases" Bone 35:892-898.

Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Adherent Technique).

Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Novel Technique).

Koh et al (2005) "Co-Culture of Human CD34+ Cells with Mesenchymal Stem Cells Increases the Survival of CD34+ Cells Against the 5-Aza-Deoxycytidine- or Trichostatin A-Induced Cell Death" Biochem. Biophys. Res. Commun. 329:1039-1045.

Kortelainen and Särkioja (1990) "Fatal Complications of Intramuscular and Intra-Articular Injections" Z Rechtsmed. 103:547-554.

Kravitz et al. "How Do Muscles Grow", IDEA Fitness Journal; 3(2), 23-25 (2006) (http://www.unm.edu/˜kravitz/Article%20folder/musclesgrowLK.html).

Laiho and Kotilainen (2001) "Septic Arthritis Due to *Prevotella bivia* After Intra-Articular Hip Joint Injection" Joint Bone Spine 68:443-444.

Lange et al (2007) "Accelerated and Safe Expansion of Human Mesenchymal Stromal Cells in Animal Serum-Free Medium for Transplantation and Regenerative Medicine" Journal of Cellular Physiology 213(1):18-26.

Luis A. Solchaga et al (2002) "Treatment of Osteochondral Defects with Autologous Bone Marrow in a Hyaluronan-Based Delivery Vehicle", Tissue Engineering, vol. 8, No. 2, pp. 333-347.

Luyten (2004) "Mesenchymal Stem Cells in Osteoarthritis" Curr. Opin. Rheumatol. 16:599-603.

Magne et al (2005) "Mesenchymal Stem Cell Therapy to Rebuild Cartilage" Trends Mol. Med. 11(11):519-526.

Martineau et al (2004) "Effects of Calcium and Thrombin on Growth Factor Release from Platelet Concentrates: Kinetics and Regulation of Endothelial Cell Proliferation" Biomaterials 25:4489-4502.

Medina et al (2000) "Purification of Human Tonsil Plasma Cells: Pre-Enrichment Step by Immunomagnetic Selection of $CD31^+$ Cells" Cytometry 39(3):231-234.

Mezey et al and Castro et al (2003) "Comment on and Response to Comment on Failure of Bone Marrow Cells to Transdifferentiate into Neutral Cells In Vivo" Science 299:1184b-1184c.

Miyata et al (2005) "Platelet-Derived Growth Factor-BB (PDGF-BB) Induces Differentiation of Bone Marrow Endothelial Progenitor Cell-Derived Cell Line TR-BME2 into Mural Cells, and Changes the Phenotype" J. Cell. Physiol. 204:948-955.

Morshed et al (2004) "Septic Arthritis of the Hip and Intrapelvic Abscess Following Intra-Articular Injection of Hylan G-F 20. A Case Report" J. Bone Joint Surg. Am. 86:823-826.

Munirah et al (2008) "Autologous Versus Pooled Human Serum for Articular Chondrocyte Growth" Journal of Orthopedic Surgery 16(2):220-229.

Müller et al (2006) "Animal Serum-Free Culture Conditions for Isolation and Expansion of Multipotent Mesenchymal Stromal Cells from Human BM" Cytotherapy 8(5):437-444.

Murphy et al (2003) "Stem Cell Therapy in a Caprine Model of Osteoarthritis" Arthritis Rheum. 48(12):3464-3474.

Murray et al (1999) "CD109 is Expressed on a Subpopulation of $CD34^+$ Cells Enriched in Hematopoietic Stem and Progenitor Cells" Exp. Hematol. 27:1282-1294.

Nakayama et al (2000) "Evaluation of Glycosaminoglycans Levels in Normal Joint Fluid of the Knee" J. Nippon Med. Sch. 67(2)92-95.

Nielsen et al (1990) "Postoperative Discitis. Radiology of Progress and Healing" Acta Radiol. 31(6):559-563.

Olweus et al (1995) "CD64/Fc Gamma RI is a Granulo-Monocytic Lineage Marker on CD34+ Hematopoietic Progenitor Cells" Blood 85(9):2402-2413.

(56) References Cited

OTHER PUBLICATIONS

Onofrio (1980) "Intervertebral Discitis: Incidence, Diagnosis, and Management" Clin. Neurosurg. 27:481-516.
Ordog et al (2004) "Purification of Interstitial Cells of Cajal by Fluorescence-Activated Cell Sorting" Am. J. Physiol. Cell Physiol 286(2):448-456.
Orpen and Birch (2003) "Delayed Presentation of Septic Arthritis of a Lumbar Facet Joint after Diagnostic Facet Joint Injection" J. Spinal Disord. Tech. 16(3):285-287.
Oshima et al (2004) "Fate of Transplanted Bone-Marrow-Derived Mesenchymal Cells During Osteochondral Repair using Transgenic Rats to Simulate Autologous Transplantation" OsteoArthritis Cartilage 12:811-817.
Otawa et al (2000) "Comparative Multi-Color Flow Cytometric Analysis of Cell Surface Antigens in Bone Marrow Hematopoietic Progenitors Between Refractory Anemia and Aplastic Anemia" Leukemia Research 24:359-366.
Park et al (2005) "Thoughts and Progress, Tissue-Engineered Cartilage Using Fibrin/Hyaluronan Composite Gel and its In Vivo Implantation" Artif. Organs 29(10):838-860.
Pellaton et al (1981) "Spectic Arthritis Following Repeated Intraarticular Injections of Glycosaminoglycanpolysulfat (Arteparon®) and Steroids for Osteoarthrosis of the Knee Joint" (French, English Abstract Only) Schweiz. Rudnsch. Med. Prax. 70(52):2364-2367.
Pietramaggiori et al (2006) "Freeze-Derived Platelet-Rich Plasma Shows Beneficial Healing Properties in Chronic Wounds" Wound Rep. Reg. 14:573-580.
Ponte and McDonald (1992) "Septic Discitis Resulting from *Escherichia coli* Urosepsis" J. Fam. Pract. 34(6):767-771.
Prins et al (1982) "Effect of Purified Growth Factors on Rabbit Articular Chondrocytes in Monolayer Culture. II. Sulfated Proteoglycan Synthesis" Arthritis & Rheumatism, 25(10):1228-1238.
Rasmusson et al (2003) "Mesenchymal Stem Cells Inhibit the Formation of Cytotoxic T Lymphocytes, but Not Activated Cytotoxic T Lymphocytes or natural Killer Cells" Transplantation 76 (8):1208-1213.
Reddi and Cunningham (1990) "Bone Induction by Osteogenin and Bone Morphogenetic Proteins" Biomaterials 11:33-34.
Regenexx™ PR article published Nov. 8, 2007; downloaded May 14, 2012.
Richardson et al (2006) "Intervertebral Disc Cell-Mediated Mesenchymal Stem Cell Differentiation" Stem Cells 24:707-716.
Roberts et al (2003) "Autologous Chondrocyte Implantation for Cartilage Repair: Monitoring its Success by Magnetic Resonance Imaging and Histology" Arthritis Research and Therapy 5(1):R60-R73.
Rolf et al (1999) "Intra-Articular Absorption and Distribution of Ketoprofen After Topical Plaster Application and Oral Intake in 100 Patients Undergoing Knee Arthroscopy" Rheumatology 38:564-567.
Ruszymah (2004) "Autologous Human Fibrin as the Biomaterial for Tissue Engineering" Med. J. Malaysia 59 Suppl.B:30-1.
Sah et al "Effects of Fibrin Glue Components on Chondrocyte Growth and Matrix Formation," in 49th Annual Meeting of the Orthopaedic Research Society, poster #0721, dated 2003.
Sanchez et al (2003) "Is Platelet-Rich Plasma the Perfect Enhancement Factor? A Current Review" Int. J. Oral Maxillofac. Implants 18:93-103.
Sato et al (1999) "Reversible Expression of CD34 by Murine Hematopoietic Stem Cells" Blood 94(8):2548-2554.
Schallmoser et al (2007) "Human Platelet Lysate Can Replace Fetal Bovine Serum for Clinical-Scale Expansion of Functional Mesenchymal Stromal Cells" Transfusion 47(8):1436-1446.
Silverman et al (Jun. 1999) "Injectable Tissue-Engineered Cartilage Using a Fibrin Glue Polymer" Plast. Reconstr. Surg. 103(7):1809-1818.
Simmons and Torok-Storb (1991) "CD34 Expression by Stromal Precursors in Normal Human Adult Bone Marrow" Blood 78(11):2848-2853.

Singer et al (1987) "Simian Virus 40-Transformed Adherent Cells From Human Long-Term Marrow Cultures: Cloned Cell Lines Produce Cells with Stromal and Hematopoietic Characteristics" Blood 70(2):464-474.
Singer et al (1984) "Evidence for a Stem Cell Common to Hematopoiesis and its In Vitro Microenvironment: Studies of Patients with Clonal Hematopoietic Neoplasia" Leuk. Res. 8(4):535-545.
Spaggiari et al (2006) "Mesenchymal Stem Cell-Natural Killer Cell Interactions: Evidence that Activated NK Cells are Capable of Killing MSCs, Whereas MSCs can Inhibit IL-2-Induced NK-Cell Proliferation" Blood 107(4):1484-1490.
Stacey et al (2000) "Randomised Double-Blind Placebo Controlled Trial of Topical Autologous Platelet Lysate in Venous Ulcer Healing" Eur. J. Vasc. Endovasc. Surg. 20:296-301.
Terstappen et al (1991) "Sequential Generations of Hematopoietic Colonies Derived From Single Nonlineage-Committed CD34+CD38-Progenitor Cells" Blood 77(6):1218-1227.
Toba et al (1999) "Novel Technique for the Direct Flow Cytofluorometric Analysis of Human Basophils in Unseparated Blood and Bone Marrow, and the Characterization of Phenotype and Peroxidase of Human Basophils" Cytometry 35(3):249-259.
Tondreau et al (2004) "Isolation of BM Mesenchymal Stem Cells by Plastic Adhesion or Negative Selection: Phenotype, Proliferation Kinetics and Differentiation Potential" Cyrotherapy 6(4):372-379.
Tosh et al (2002) "Conversion of Pancreatic Cells to Hepatocytes" Biochem. Soc. Trans. 30:51-55.
Ueda et al (2007) "Induction of Senile Osteoporosis in Normal Mice by Intra-Bone Marrow-Bone Marrow Transplantation from Osteoporosis-Prone Mice" Stem Cells 25(6):1356-1363.
Weber (1988) "Infectious Damage to the Intervertebral Disk—Before and Following Discotomy" Z. Orthop Ihre Grenzeb 126(5):555-562 (German, English Abstract Only).
Willems et al (Jun. 2004) "Lumbar Discography: Should we Use Prophylactic Antibiotics? A Study of 435 Consecutive Discograms and a Systematic Review of the Literature" J. Spinal Disord. Tech. 17(3):243-247.
Willheim et al (1995) "Purification of Human Basophils and Mast Cells by Multistep Separation Technique and mAb to CDw17 and CD117/c-kit" J. Immunological Methods 182:115-129.
Xaymardan et al (2004) "Platelet-Derived Growth Factor-AB Promotes the Generation of Adult Bone Marrow-Derived Cardiac Myocytes" Circ Res. 94(5):E39-E45.
Yamada et al (2003) "Bone Regeneration Following Injection of Mesenchymal Stem Cells and Fibrin Glue with a Biodegradable Scaffold" J. Cranio-Maxillofac. Surg. 31:27-33.
Yang et al (1994) "Cardioprotective Effects of Platelets Against Ischaemia-Reperfusion Injury are Related in Part to Platelet Glutathione Redox Cycle" Cardiovasc. Res. 28(10):1586-1593 Abstract.
Ye et al (2007) "Effect of Three Growth Factors on Proliferation and Cell Phenotype of Human Fetal Meniscal Cells" Chinese Journal Reconstructive Surgery 21(10):1137-1138 with English Abstract.
Zhu et al (2001) "Recombinant Human Acidic Fibroblast Growth Factor Accelerates the Healing of Full-Thickness Dermal Wounds in Pigs" Modern Rehabilitation 5(9):31 with English Abstract.
Zhu et al (2006) "Hypoxia and Serum Deprivation-Induced Apoptosis in Mesenchymal Stem Cells" Stem Cells 24:416-425.
PR Newswire (2013) "NeuroTherm Acquires Smith & Nephew Interventional Spine Pain Management Assets" Database [Online] Arpil 7. Available Web Site: http://www.prnewswire.com/news-releases/neurotherm-acquires-smith--nephew-interventional-spine-pain-management-assets-89991457.html Last Update: Unknown Accessed on: Nov. 21, 2013.
Smith & Nephew Home Page (2009) "Smith & Nephew launches TRUCATH Spinal Injection System" Database [Online] Sep. 28. Available Web Site: http://www.smith-nephew.com/news-and-media/news/smith-and-nephew-launches-trucath-spinal-injectio/ Last Update: Unknown Accessed on: Nov. 21, 2013.

* cited by examiner

COMPOSITIONS AND METHODS TO PROMOTE IMPLANTATION AND ENGRAFMENT OF STEM CELLS

CROSS REFERENCE TO RELATED APPLICATION

This application is a continuation of pending U.S. patent application Ser. No. 12/809,445, filed Nov. 8, 2010 by Christopher J. Centeno and entitled, "Compositions and Methods to Promote Implantation and Engrafment of Stem Cells," which application claims the benefit of International Application No. PCT/US08/87452, filed Dec. 18, 2008, entitled "Compositions and Methods to Promote Implantation and Engrafment of Stem Cells," which application claims the benefit of U.S. Provisional Application Ser. No. 61/014,987, filed Dec. 19, 2007, entitled "Compositions to Promote Implantation and Engrafment of Stem Cells," each of which is incorporated herein by reference in its entirety.

TECHNICAL FIELD

The invention generally relates to compositions and methods for induction of tissue repair in a patient in need thereof. More particularly, the invention relates to compositions and methods for inducing diffuse micro-tissue injury and enhanced cell growth at a site to facilitate in-vivo tissue repair and/or replacement in a patient in need thereof.

BACKGROUND OF THE INVENTION

Mesenchymal stem cells (MSCs) are pluripotent blast or embryonic-like cells located in blood, bone marrow, dermis and periosteum. In general these cells are capable of renewing themselves over extended periods of time as well as, under various environmental conditions, differentiating into cartilage, bone and other connective tissue. Recently, various investigators have researched the potential for using these cells to repair or regenerate target tissues, e.g., bone, cartilage, cardiac muscle, etc. In this manner MSCs have been reported to have regenerative capabilities in a number of animal models. See Acosta et al. (2005) Neurosurg Focus 19(3):E4; Barry (2003) Novartis Found Symp. 249:86-102, 170-4, 239-41; Brisby et al. (2004) Orthop Clin. North Am. 35(1):85-89; Buckwalter and Mankin (1998) Instr Course Lect. 47:487-504; Caplan (1991) J Orthop Res. 9(5):641-650.

Recent research has shown that tissue injury can act as a homing signal for bone marrow derived MSCs to migrate to the site of injury. (Agung et al., Knee Surg. Sports Traumatol Arthrosc, 2006, 14(12):1307-14). However, these studies utilized a surgical approach to include a gross tissue injury which was shown to signal MSCs to the injury site, this approach is, however, likely impractical for clinical care (for example cutting portions of an ACL ligament to signal MSC homing to the ACL site could result in more damage than actual repair to the ACL). Note also that other researchers have discussed the possibility that tissue injury can act as a homing signal for MSCs into various tissues. (Ramirez et al., Br J Sports Med., 2006 40(8):719-22; Shyu et al., Front Biosci., 2006 11:899-907).

In addition, injectable hyperosmolar substances that initiate tissue injury and potentially prompt healing in a clinical setting have been utilized to varying success. (Centeno et al., Pain Physician, 2005, 8(1):67-72; Mooney, V., Spine J, 2003 3(4):253-4; Reeves et al., J Altern Complement Med., 2000 6(4):311-20; and Reeves et al., Altern Ther Health Med 2000 6(2):68-74). However, these procedures have had limited practical success in the health care setting.

Clinical advantage could be gained through minimally invasive medical procedures that impart stem cells to a site of need within a patient (for example, percutaneous injection of MSCs to a site in need). Unfortunately, mere implantation of stem cells to a site in this manner has proven mostly ineffective. As such, there is a need in the health care setting to more optimally utilize stem cell implants as well as to facilitate repair of sites in a patient without first grossly injuring the site to initiate a repair process.

Against this backdrop the present invention was developed.

SUMMARY OF THE INVENTION

The present invention provides repair compositions for facilitating tissue repair and/or replacement in a patient in need thereof. Repair compositions include an effective amount of a cell growth enhancing composition in combination with one or more inflammation inducing agent(s).

Aspects of the cell growth enhancing composition include the use of autologous and/or non-autogous cell growth enhancing materials. Cell growth enhancing compositions can include an autologous composition spiked with one or more non-autologous factors. Typical autologous cell growth enhancing compositions include platelet rich fibrin solutions, e.g., 5% to 40% platelet lysate solutions, and/or platelet gels. Typical non-autologous growth compositions include recombinant growth factors such as insulin-like growth factor.

Aspects of the inflammation inducing agents include agents that induce local micro-diffuse injury at the site in need of repair and include osmolar agents, inflammatory cytokines, and/or sclerosing agents. In some aspects combinations of these agents can be utilized, for example a combination of osmolar agents with a sclerosing agent.

Repair compositions of the invention can further include essential nutrients useful for the site in need of repair, for example collagen where the repair site is a knee joint in need of cartilage repair. In addition, repair compositions can include anabolic hormones, like human growth hormone, for further tissue growth signaling in the repair site.

Finally, repair compositions of the invention can include stem cells and in particular isolated stem cells, for example, isolated autologous or non-autologous mesenchymal stem cells. Stem cells can be delivered to the site in the repair composition or separately from the repair composition, i.e., both separated physically and temporally.

The present invention also provides methods for facilitating tissue repair in a patient in need thereof. Methods include harvesting and preparing a repair composition, e.g., a 5% to 40% platelet lysate from a patient having a repair site in need of treatment and an inflammation inducing agent; administering to the repair site the repair composition (in an amount necessary to endure and maintain repair) in accordance with embodiments of the invention described herein; and optionally administering stem or other like repair cells to the repair site to facilitate tissue repair at the site in need thereof. In some aspects of the methods herein, the repair composition is a first inflammation inducing agent composition and a second cell growth enhancing composition, where the first composition is administered to the repair site to induce local microtissue injury followed by administration of the second composition to enhance cell growth at the same site. In some instances, stem cells or other repair-like cells are administered to the site to enhance the repair process, typically with or shortly after administration of the cell growth enhancing composition. Methods herein can include multiple applications of repair compositions over the course of 1 week to 6 months.

Finally, the present invention provides pharmaceutical compositions for use in therapeutic applications. In some cases the pharmaceutical compositions are used to treat a patient with a site of injury in need of repair and in some cases the patient has osteoarthritis, osteoporosis or other like degenerative disease.

These and various other features and advantages of the invention will be apparent from a reading of the following detailed description and a review of the appended claims.

DETAILED DESCRIPTION OF THE INVENTION

Embodiments of the present invention provide repair compositions for facilitating tissue repair and/or tissue replacement in a patient in need thereof. For purposes herein a patient refers to any mammal and preferably human having a need for the compositions and/or methods of the present invention. In one embodiment, repair compositions include a therapeutically effective amount of a cell growth enhancing composition in combination with one or more inflammation inducing agents.

Embodiments of the invention include repair compositions where the cell growth enhancing composition is an autologous or non-autologous growth factor(s), including, for example, recombinant growth factors. In other embodiments the cell growth enhancing composition is a mixture of autologous and non-autologous growth factor(s).

In typical embodiments the cell growth enhancing composition is one or more autologous growth factor(s) from the patient in need thereof, i.e., the patient having the site of injury in need of repair. Cell growth enhancing growth factor can include autologous platelet and/or platelet lysate composition(s).

Embodiments of the invention further include repair compositions where the inflammation inducing agent(s) is an agent capable of inducing micro-tissue or localized injury at the site where tissue repair is required. Inflammation inducing agents for use herein include osmolar agents, inflammatory cytokines, sclerosing agents, and the like. As such, a repair composition can include an autologous platelet lysate combined with one or more inflammation inducing agents.

Repair compositions of the present invention can be administered through a surgical incision, arthroscopically and/or percutaneously. A site of repair in a patient for purpose of the present invention is any site in need of tissue repair or re-growth, for example a knee in need of cartilage, a liver in need of hepatocytes, a bone in need of osteocytes, etc.

Embodiments of the present invention also provide methods for facilitating tissue repair in a patient in need thereof. Methods include administering a repair composition that includes both the cell growth enhancing composition and one or more inflammation inducing agent(s); or administering non-contemporaneously one or more inflammatory inducing agent(s) and a cell growth enhancing composition.

In one embodiment, methods include obtaining an autologous growth enhancing composition from the patient in need of tissue repair; administering an inflammatory inducing agent to the patient in an amount sufficient to induce local inflammation at the site in need of tissue repair; and administering the autologous growth enhancing composition to the patient at the site in need of tissue repair in an amount to effectively facilitate cell growth/expansion at the site. In some embodiments the inflammatory inducing agent and growth enhancing composition are administered contemporaneously via separate compositions; in other embodiments the inflammatory inducing agent and growth enhancing composition are administered within 24 to 96 hours, more preferably between 72 and 96 hours, of each other. Multiple administrations can be performed over the course of 1 to 6 months (or more dependent on health professionals determination). In other embodiments the inflammatory inducing agent and growth enhancing composition are combined and administered as one composition.

DEFINITIONS

The following definitions are provided to facilitate understanding of certain terms used frequently herein and are not meant to limit the scope of the present disclosure.

"Cell growth enhancing composition" refers to growth factors like recombinant FGF, recombinant TGF-beta, autologous compositions like platelets, platelet rich fibrin, platelet rich plasma, platelet lysate, platelet gels, and the like and can include growth factors, cytokines, hormones, essential nutrients or other proteins, fatty acids, or carbohydrates.

"Inflammation inducing agent" refers to any agent capable of inducing diffuse micro-tissue injury at a site, including osmolar agents like hypertonic dextrose, inflammatory cytokines, e.g., MIP-1, MIP-1$\alpha$, MIP-1$\beta$, and MIP-2, sodium morrhuate, pumice and phenol.

"Mesenchymal stem cell" or "MSCs" refers to multipotent stem cells capable of differentiating into osteoblasts, chondrocytes, myocytes, adipocytes, neuronal cells, pancreatic islet cells, and the like (see below). Source MSCs of the invention are typically harvested from the iliac crest of the patient in need of the repair (or a suitable donor, (non-autologous)), such patient is referred to herein as a "patient in need thereof" (note that other sources, such as adipose tissue, synovial tissue, and connective tissue have recently been identified and are also considered as MSC sources within the scope of the present invention). In one embodiment, approximately 10-20 cc of bone marrow is harvested and "isolated" using methods described in U.S. Patent Application 60/761,441 to Centeno or through adherence to plastic, as described in U.S. Pat. No. 5,486,359 to Caplan et al. Each of these references is incorporated herein in their entirety for all purposes.

"Platelet lysate" refers to the combination of natural growth factors contained in platelets that has been released through lysing of the platelets. This can be accomplished through chemical means (i.e. $CaCl_2$), osmotic means (use of distilled $H_2O$), or through freezing/thawing procedures. Platelet lysates of the invention can also be derived from whole blood and can be prepared as described in U.S. Pat. No. 5,198,357, which is incorporated by reference herein. Alternatively, platelet lysate for use herein can be prepared from a bone marrow harvest using the method of Doucet (Doucet, Ernou et al., 2005, Journal of Cellular Physiology, 205(2): 228-236), which is incorporated by reference herein in its entirety). Typical lysates include from about tens of millions to 100's of billions platelets. As shown by Martineau et al., Biomaterials, 2004 25(18) p4489-503 (incorporated herein by reference in its entirety), platelet lysates inherently include the growth factors required to facilitate consistent MSC growth. In typical embodiments the platelet lysate is autologous and is in an amount useful for effective and consistent use in embodiments herein. In particular, it should be noted that while the levels of growth factors such as TGF-beta are much lower in platelet lysate than those commonly used in vitro to expand MSCs, it is believed that there are significant synergistic effects when all of the low level growth factors contained in platelet lysate are used together.

"Protein," "peptide," and "polypeptide" are used interchangeably to denote an amino acid polymer or a set of two or more interacting or bound amino acid polymers.

"Stem cells" refers to any cell having the characteristic of being unspecialized and able to renew for extended periods of time through cell division and being inducible to become cells with specialized function.

Tissue Repair Compositions of the Invention

Compositions of the invention include tissue repair compositions having enhanced capacity for tissue repair and/or replacement in a patient in need thereof. Compositions typically include two different aspects, a first aspect is directed toward induction of a local inflammatory response at the site where tissue repair is required (in some cases due to cell lysis caused by the inflammatory agent(s)); and a second aspect directed at facilitating cell growth (autologous or non-autologous cell growth enhancing materials) at the same site. The combination of inflammation and cell growth induction is more impressive and unexpected than convention tissue repair methodologies. In some embodiments a third aspect is included, autologous or non-autologous stem cells for facilitating the repair composition capacity to repair or replace tissue at a site in need.

Typical repair compositions herein include combinations of at least one or more inflammation inducing agent(s) with at least one or more cell growth enhancing composition(s). In one embodiment the cell growth enhancing composition(s) for use herein can include one or more autologous factor(s). In another embodiment the cell growth enhancing compositions(s) for use herein can include one or more non-autologous factor(s). In other embodiments the repair compositions include a combination of autologous and non-autologous growth factors.

Typical autologous growth factors used herein include: platelets, platelet rich plasma, platelet rich fibrin, platelet lysate, or mixtures thereof.

As described herein, typical non-autologous factors include recombinant growth factors, e.g., epidermal growth factor, fibroblast growth factor-2, vascular endothelial growth factor, insulin-like growth factor, transforming growth factor-β and platelet-derived growth factor. Recombinant growth factors can be purchased from various manufacturers (e.g., RDJ, Inc., Bio Vision Inc., Bio Clone Inc., etc.) or through known isolation and purification techniques.

In addition, repair compositions of the invention can include autologous growth factor compositions enriched with recombinant growth factors, for example, a platelet lysate prepared from the patient in need of tissue repair spiked with recombinant transforming growth factor-β.

Embodiments herein can include repair compositions having one or more inflammation inducing agents. Inflammatory inducing agents as defined herein are agents that induce local cell injury, in some cases the inflammation inducing agent is hypertoxic dextrose, sodium morrhuate, pumice, phenol, and/or one or more inflammation inducing cytokine(s). Inflammation inducing cytokines for use herein include macrophage inflammation protein-1 (MIP-1), MIP-1α, MIP-1β, and MIP-2.

In one embodiment, a patient is treated with a repair composition that includes 5-50% hypertonic dextrose. In a second embodiment, a patient is treated with a repair composition that includes a dose of 1%-10% sodium morrhuate. Finally, repair compositions can include phenol and be used in a patient in need thereof at a dose of from about 1%-20%. The total volume of this aspect of the invention can be variable but can be from 1 to 5 milliliters per administration of the agent.

In addition, inflammation inducing agents of the invention can include materials that exacerbate a local injury and thereby increase the effectiveness of the repair compositions of the invention. Materials used herein include gels, hydrogels, and foams. In some cases the gels, hydrogels and/or foams are bioabsorbable. These high density mixtures can then be diluted by the body's own repair response or can be diluted back to the 0.9% physiologic range by a subsequent treatment of normal saline. Thus, for example, repair compositions can include agents that exacerbate local injury (gels, hydrogels, foams) which may be combined with other inflammation inducing agents, including hypertoxic dextrose, sodium morrhuate, phenol and the like.

In typical embodiments the repair composition includes a cell growth enhancing composition of an autologous growth factor, for example a platelet lysate. A platelet lysate between from about 5% to about 40% and more typically between 5% and 20% is preferred, although other concentrations can be used. Platelet lysate solutions can be obtained and prepared according to the methods and compositions as described in U.S. patent application Ser. No. 11/773,774, which is incorporated herein by reference for all purposes (other methodologies have been discussed previously). Total volume of prepared platelet lysate administered to a patient can be from 1 ml to 40 ml and in some cases 1 ml to 20 ml.

One problem with clinical use of platelet lysate in a patient is the variability in the bioavailability and concentrations of growth factors in the particular platelet lysate. As a result, without specific biological assays to determine factor levels in the lysate, dosing lysate becomes difficult. Research discussed in U.S. patent application Ser. No. 11/773,774 clearly showed that some patients yielded maximum possible in-vitro expansion in 5% lysate, while others required up to a 400% increase in concentration of PL to achieve maximum expansion. Even if assays of growth factors were clinically available and commonly used, the bioavailablility of these growth factors would still be difficult to access.

In this case, the availability of culture expansion data with this patient's platelet lysate provides data about the activity of these growth factors (as discussed in U.S. patent application Ser. No. 11/773,774 and incorporated by reference). This data can be used to identify the optimal platelet lysate % for use in a target patient, i.e., culture autologous MSCs with variable amounts of autologous platelet lysate.

Repair compositions of the invention can further include essential nutrients to further enhance tissue repair, for example collagen, glycoaminosglycan's, amino acids, peptides, proteins, sodium pyruvate, glucose, glutamine, ribonucleosides, deoxyribonucleosides, carbohydrates, essential oils, and the like. As such, a platelet lysate solution can be spiked with collagen and various amino acids to facilitate the repair process in the patient.

Repair compositions of the invention can also include anabolic hormones, for example, human growth hormone, testosterone, and the like. Again, for example, a platelet lysate could be spiked with a target anabolic hormone prior to administering to the patient in need thereof.

Finally, repair compositions as described herein can include autologous or non-autologous stem cells to enhance repair and re-growth of the repair site. In one embodiment, mesenchymal stem cells (MSCs) are prepared and expanded in accordance with U.S. patent application Ser. No. 11/773,774, (incorporated by reference previously), and implanted to the repair site. Note that other stem cell or cell types are within the scope of the present invention, however, MSCs are identified as one potential embodiment herein.

Recently, Centeno et al. (U.S. patent application Ser. No. 11/773,774) described a method for expanding MSCs using a growth channel and autologous platelet lysate. Also described were methods for transplanting certain levels of growth factors (platelet lysate or platelets) with the expanded MSCs to the area in a patient in need of repair. The levels of these growth factors were based on a percentage of platelet lysate needed to optimally expand certain cells ex-vivo. These techniques can also be utilized to provide a sufficient number of MSCs for administration to the patient in need.

Method of Facilitating Tissue Repair in a Patient in Need Thereof:

Embodiments described herein include methods for the therapeutic restoration of a site in a patient in need thereof. For example, therapeutic restoration of a degenerative disc or cartilage of a joint in need thereof. Other examples include the replacement of cardiac muscle in the heart.

Methods herein include initially determining parameters for optimally treating a patient's repair site. For example, a determination of what and how much inflammation inducing agent(s) would work best at the site of injury as well as to determine what and how much cell enhancing growth composition should be used (autologous, non-autologous, mixture, etc). In this regard, the site should have enough micro injury to direct cellular repair mechanisms without causing more macro injury to the site which is incapable of healing. In addition, a determination on whether a repair composition of the invention would be used, or whether an inflammation inducing agent composition would be used initially followed by contact with a cell growth enhancing composition. Administration of the repair composition to the site of repair in the patient is then followed by injury site analysis.

Therapeutic Applications

Repair compositions of the invention provide optimal repair conditions/environment to a repair site in a patient in need thereof. Repair compositions both induce micro-tissue injury, thereby signaling the patient's inflammatory factors and additionally initiate and/or facilitate cell growth at the site. In some embodiments, ex-vivo cultured stem cells are implanted into the environment to further increase the potential success of repair at the repair site.

Repair compositions herein can be formulated as pharmaceutical compositions and administered to a patient in need thereof, preferably a mammalian host, including a human patient. Repair compositions can be formulated in a variety of forms adapted to the chosen route of administration.

Embodiments herein include repair compositions that include a pharmaceutically acceptable carrier and/or specific delivery drug.

For administration of the composition as an injectable solution or suspension, repair compostitions can be formulated according to techniques well-known in the art, using suitable dispersing or wetting and suspersing agents, such as sterile oils, including synthetic mono- or diglycerides, and fatty acids, including oleic acid.

Soutions or suspensions of the repair compositions can be prepared in water, isotonic saline (PBS), and optionally mixed with a nontoxic surfactant. Dispersions may also be prepared in glycerol, liquid polyethylene, glycols, vegetable oils, triacetin and mixtures thereof. Under customary use and storage conditions, the repair compositions herein may contain one or more preservatives to prevent growth of microorganisms.

Therapeutic applications herein, refers to use of the compositions and methods of the invention to treat a patient having a site of injury in need of tissue repair. Sites of injury in need or repair, i.e., repair sites, include joints in need or cartilage repair and/or regrowth, bone in need of bone repair or regrowth, tendon/ligament in need of repair or regrowth, organ repair in need of functional cell repair and/or regrowth (for example, cardiac muscle growth in a heart), and the like.

In some embodiments, the invention is directed at therapeutic applications for patients having disease states that limit their inherent ability to repair or re-grow cells in a repair site. For example, patient's having osteoarthritis, osteoporosis, avascular necrosis, would all benefit from the facilitated repair compositions and methods of the present invention.

This invention focuses on creating conditions that mimic inflammation to induce tissue repair. Most animal research in this arena has been performed in acute injury models (meaning an injury is experimentally created and is still acute or sub-acute when MSCs are introduced to promote tissue repair). This is a poor surrogate for a chronic osteoarthritis model where no acute injury exists. The inventor's research in this area has shown that the creation of an acute osmolar micro injury can assist in MSC related meniscus repair (see Example 1). In these cases we used percutaneously delivered hypertonic dextrose to initiate an injury and followed this with the percutaneous delivery of culture expanded MSCs (expansion carried out per U.S. patent application Ser. No. 11/773,774 incorporated by reference for this purpose).

Having generally described the invention, the same will be more readily understood by reference to the following examples, which are provided by way of illustration and are not intended as limiting.

EXAMPLES

Example 1

Therapeutic use of Embodiments of the Present Invention

Approximately 20 ml of whole bone marrow was extracted from two patients, CD (40 year old, white male) and JV (28 year old, white male). CD held a pre-op diagnosis of severe osteoarthritis of the knee with evidence of myxoid degeneration of the medial>lateral meniscus and JV held the pre-op diagnosis of a chronic bucket handle tear of the posterior horn of the medial meniscus.

Each patient was then placed prone on an OR table and the area to be harvested was numbed with 1% Lidocaine, and a sterile disposable trocar was used to draw 10 cc of marrow blood from the right PSIS area and 10 cc from the left PSIS area.

Whole marrow was centrifuged at 100 g for 4-6 minutes to separate the plasma from the RBCs. The plasma was removed, placed in a separate tube, and centrifuged at 1000 g for 10 minutes to pellet the nucleated cell fraction. The nucleated cells were washed once in PBS, counted, and then resuspended in DMEM+10% platelet lysate (PL) and seeded at $1 \times 10^6$ cells/cm$^2$ in monolayer flask culture. Cultures were incubated at 37° C./5% $CO_2$ in a humidified environment. The culture medium was changed after 3 days, removing the majority of the non-adherent cell population. MSC colonies developed 6-12 days after seeding. After growing to near confluence, the colonies were trypsinized over 30-60 seconds such that only the colony-forming MSCs detached. The MSCs were reseeded at a density of 12,000 cells/cm$^2$ in DMEM+5%, 10%, or 20% PL. Each culture was passaged 1:3 after reaching 40-50% confluence. After MSCs had been grown to the $3^{rd}$-$5^{th}$ passage, they were suspended in phosphate buffered saline (PBS). The patient was brought back to clinic and was consented in writing.

The following operative course was taken:
1. Each patient was first treated with 12.5% dextrose (hyper-osmolar agent) and local anesthetic injected intra-articular via c-arm through a medial inferior port of the involved knee.
2. 3-5 days later, after the acute inflammatory response had subsided from the initial injection, culture expanded autologous MSCs in PBS were injected with 10% platelet lysate.

Modified VAS questionnaires and Functional Rating Index questionnaires were provided to the patient and administered before the procedure, 1 month after the procedure, and three months after the procedure. Range of motion measurements of the knee were measured by a physical therapist before the procedure, 1 month post-procedure and 3 months post procedure. In addition, pre-procedure MRI's were obtained on a GE 3.0 T magnet with Proton Density Fast Spin sequences in the sagittal coronal planes. Post procedure images at 1 month and at 3 months were obtained using mating excitation times (NEX), repetition times (TR), and echo times (TE). Quantitative meniscus and articular cartilage volume analysis was carried out using commercially available image processing software (OSIRIS-Digital Imaging Unit, Division of Medical Informatics, University Hospital of Geneva) using three traces by the same examiner of each region of interest (ROI). Standard deviation from the mean was calculated for these three traces. The area of the medial weight bearing femoral defect was also traced and calculated in a similar manner. Results (See Table 1):

The results from the example show the surprising effectiveness of embodiments of the invention and the utility of using compositions and methods in accordance with the present invention.

Example 2

MSCs Expand in Presence of Dextrose

To ensure that the various growth factors commonly found in platelet lysate (TGF-beta, FGF, IGF, PDGF) could be exposed to a hypertonic environment and still function to support mesenchymal stem cell growth, the following experiment was carried out with culture expanded human MSCs:

Method:

To 0.8 mL of 10% platelet lysate was added 0.2 mL of 50% Dextrose. In a separate condition, to 0.8 ml of 10% platelet lysate (PL) we added 0.2 mL of Phosphate Buffered Saline. We allowed the two samples to incubate 1 hr at 37 C in a 5% $CO_2$ environment. 1 mL of each suspension was then removed and added to 9 mls of basic alpha mem media to get final ratio of 10% PL and 1% Dextrose. Each well of a 6 well plate was then seeded with 100,000 cells in each suspension. After 48 hr incubation all of the cells appeared morphologically normal.

TABLE 1

MRI volume changes in femoral cartilage and meniscus from pre-procedure, 1 month post procedure, 3 months post procedure, and 6 months post procedure:

| Patient Name | Joint | Time | Area of Measurement | Volume e(n = 3) | STDEV | SE | Cell # Injected (millions) | % Change from Pre-injection |
|---|---|---|---|---|---|---|---|---|
| 1. | L Knee | Pre-injection | Cartilage surface | 4535 | 215.37 | 124.49 | 32.66 | |
| | | | meniscus | 2646 | 126.05 | 72.86 | | |
| | | 1 month | Cartilage surface | 5484 | 128.34 | 74.19 | | 20.93 |
| | | | meniscus | 3233 | 95.35 | 55.11 | | 22.18 |
| | | 3 months | Cartilage surface | 4867 | 378.02 | 218.51 | | 7.32 |
| | | | meniscus | 2979 | 154.44 | 89.27 | | 12.59 |
| | | 6 months | Cartilage surface | 5531 | 120.97 | 69.93 | | 21.96 |
| | | | meniscus | 4055 | 168.57 | 97.44 | | 53.25 |
| 2. | R Knee | Pre-injection | Cartilage surface | 7994 | 113.51 | 65.61 | 20.9 | |
| | | | meniscus | 2512 | 178.5 | 103.18 | | |
| | | 1 month | Cartilage surface | 8150 | 131.04 | 75.75 | | 1.95 |
| | | | meniscus | 2632 | 126.65 | 73.21 | | 4.78 |
| | | 3 months | Cartilage surface | 9121 | 468.93 | 271.06 | | 14.10 |
| | | | meniscus | 3322 | 246.55 | 142.51 | | 32.25 |

| PL+ | PL− | Average | Std Dev | CV |
|---|---|---|---|---|
| 2.50E+05 | 1.90E+05 | 2.20E+05 | 30000 | 13.636 |

Results:
PL+ = with Dextrose
PL− = control

The example shows that MSCs can be effectively expanded in the presence of dextrose (inflammatory inducing agent), a surprising and unexpected result.

What is claimed is:

1. A method for facilitated tissue repair in a subject in need thereof comprising:
    obtaining platelets from the subject;
    preparing a 5% to 40% platelet lysate solution from the platelets;
    administering a hyper osmolar agent to the subject in an amount sufficient to induce local inflammation at the site in need of tissue repair; and
    subsequently and non-contemporaneously administering a composition comprising the 5% to 40% platelet lysate solution to the subject at the site in need of tissue repair;
    wherein tissue repair is facilitated at the site in the subject in need of tissue repair.

2. The method of claim 1, further comprising obtaining mesenchymal stem cells (MSC) from the patient and expanding the MSC in culture, wherein the composition further comprises the patient's expanded MSC.

3. The method of claim 1, where administering to the patient is to the site in need of repair through a surgical incision, arthroscopically or percutaneously.

4. The method of claim 1, wherein cytokines are added to the 5% to 40% platelet lysate solution in amount sufficient to alter the timing of growth factor degranulation off of platelets in the platelet lysate solution.

5. The method of claim 1, wherein the composition further comprises one or more essential nutrients wherein the essential nutrients are capable of further facilitating tissue repair.

6. The method of claim 5, wherein the one or more essential nutrients is selected from the group consisting of glycoaminosglycans, collagen, amino acids, peptides, proteins, sodium pyruvate, glucose, glutamine, ribonucleosides, deoxyribonucleosides, carbohydrates, and essential oils.

7. The method of claim 1, wherein the composition further comprises one or more anabolic hormones.

8. The method of claim 1, wherein the inflammation inducing agent is formulated as a gel, hydrogel, or foam and the formulation localizes the micro-injury to the area of application.

9. The method of claim 1, wherein the site in need of tissue repair is cartilage of a joint.

10. The method of claim 9, wherein the joint is the knee joint.

11. The method of claim 1, wherein the non-contemporaneously administered composition comprising 5% to 40% platelet lysate solution is administered 3-5 days after the administration of the hyper osmolar agent.

* * * * *